United States Patent [19]

Takema et al.

[11] Patent Number: 4,743,441
[45] Date of Patent: May 10, 1988

[54] COSMETIC COMPOSITION

[75] Inventors: Yoshinori Takema, Tokyo; Rikio Tsushima, Wakayama; Yutaka Yasuda, Kaizuka; Yoshinao Kono, Wakayama, all of Japan

[73] Assignee: Kao Corporation, Tokyo, Japan

[21] Appl. No.: 907,160

[22] Filed: Sep. 15, 1986

Related U.S. Application Data

[63] Continuation of Ser. No. 662,623, Oct. 19, 1984, abandoned.

[30] Foreign Application Priority Data

Oct. 28, 1983 [JP] Japan ................. 58-202273

[51] Int. Cl.$^4$ .............. A61K 7/00; A61K 9/00; A61K 7/04; A61K 7/021; A61K 7/06; A61K 7/035; C08F 16/06
[52] U.S. Cl. ........................ 424/47; 525/60; 424/61; 424/63; 424/70; 424/69; 424/DIG. 1; 514/844; 514/845; 514/846; 514/847
[58] Field of Search ............ 525/60; 424/47, 61, 424/63, 70, 69; 514/844, 845, 846, 847

[56] References Cited

U.S. PATENT DOCUMENTS 3,553,152  1/1971  Kershaw et al. ............ 525/60
3,808,175  4/1974  Printy ...................... 424/47

FOREIGN PATENT DOCUMENTS 1588198  4/1970  France .
58-63706  4/1983  Japan ..................... 525/60

OTHER PUBLICATIONS

*Harry's Cosmeticology*, pp. 276–279 (1982).

Primary Examiner—Albert T. Meyers
Assistant Examiner—F. Krosnick
Attorney, Agent, or Firm—Oblon, Fisher, Spivak, McClelland & Maier

[57] ABSTRACT

A film-forming cosmetic composition useful as a facial pack, nail enamel, eye liner etc., which comprises a copolymer of vinyl alcohol and alkyl vinyl ether, being referred to simply as PVA/AVE, consisting of 98 to 80 mole % of vinyl alcohol monomer units and 2 to 20 mole % of linear or branched alkyl vinyl monomer units having from 1 to 6 carbon atoms. The molar ratio of the vinyl alcohol monomer units to the alkyl vinyl ether monomer units is in the range of from 95/5 to 85/15. The PVA/AVE according to the invention has no acetic groups with ester bonds in a molecule. Instead, there are alkyl or alkenyl groups having ether bonds which serve for steric hindrance for preventing gelation of an aqueous solution of such copolymer. From this reason, the PVA/AVE does not undergo any hydrolysis as time passes and is thus excellent in storage stability.

6 Claims, 1 Drawing Sheet

FIGURE
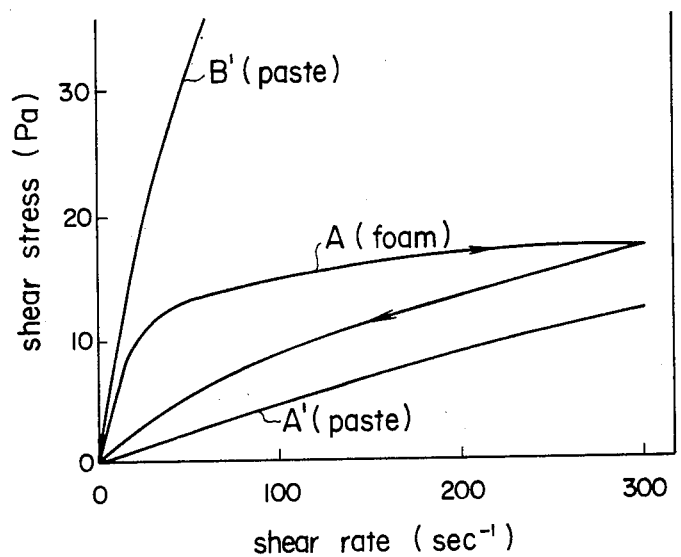

COSMETIC COMPOSITION

This application is a continuation of application Ser. No. 662,623, filed Oct. 19, 1984, now abandoned.

BACKGROUND OF THE INVENTION (i) Field of the Invention

This invention relates to cosmetics and more particularly, to film-forming cosmetics, particularly film packs, which comprise copolymers of vinyl alcohol and alkyl vinyl ethers (hereinafter referred to simply as PVA-/AVE).

(ii) Description of the Prior Art

Film-forming agents used in film packs (hereinafter referred to simply as pack(s)) are predominantly made of water-soluble polyvinyl alcohol polymers. The polyvinyl alcohol polymers are obtained by polymerizing vinyl acetate and saponifying the resulting polyvinyl acetate. Depending on the degree of saponification, the polymers can be classified into polymers in which all acetic groups are converted into hydroxyl group (completely saponified product: hereinafter referred to simply as PVA) and polymers in which most acetic groups are converted into hydroxyl groups while leaving part of the acetic groups (partially saponified product: hereinafter referred to simply as PVA/PVAc). In general, packs make use of polyvinyl alcohol resins having 10 to 20% of residual acetic groups in order to prevent gelation of the aqueous solution and impart flexibility to the film.

However, such PVA/PVAc is not stable because of the presence of non-saponified acetic groups. For instance, the acetic groups undergo hydrolysis as time passes, with attendant disadvantages that the pH of the pack lowers and the pack emits the odor of acetic acid. When the PVA/PVAc is added to packs in high concentration, the pack becomes so viscous that when applied to skin, the pack does not spread smoothly and is not suitable for application. In general, the PVA/PVAc has to be used in low concentration, with the results that drying of long time becomes necessary. PVA which is the completely saponified product is free of any objectionable odor and stable in pH, but because the aqueous solution becomes gelled, PVA is unsuitable as a film-forming agent for packs.

SUMMARY OF THE INVENTION

In view of these circumstances, it occurred to the present inventors that in order to prevent gelation from polyvinyl alcohol resins, residual groups such as acetic groups which would cause steric hindrance were necessary. If acetic groups which are likely to be hydrolyzed could be replaced by other stable groups which have steric hindrance similar to the acetic groups, stable packs could be obtained. As a result of intensive studies, it was found that PVA/AVE whose acetic ester had been substituted with alkyl ether had good characteristic as film-forming agents and when such materials were added to cosmetic compositions, excellent film-forming cosmetics could be obtained. Moreover, it was found that when this low viscosity system was utilized to make an aerosol and sprayed, it was possible to render the system having rheological characteristics thixotropic with good spreadability. It was also found that when applied to skin, the system could be spread with formation of a thin film, so that the drying time could be shortened significantly over the case of known paste packs. The present invention is accomplished on the basis of the above finding.

The present invention provides cosmetic compositions which comprise, as a main component, a copolymer of 98 to 80 mole% of vinyl alcohol monomer units and 2 to 20 mole% of linear or branched alkyl vinyl ether monomer units having from 1 to 6 carbon atoms.

BRIEF DESCRIPTION OF THE DRAWING

A sole FIGURE is a graph showing a fluidity characteristic of a foamed product A of the invention, a paste composition of the present invention and a paste composition B for comparison.

DETAILED DESCRIPTION OF THE INVENTION

The copolymer (PVA/AVE) which is the main component of the cosmetic compositions according to the invention is represented by the following general formula (I)

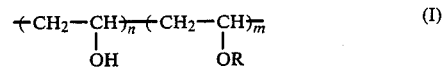

in which R represents a linear or branched alkyl group having from 1 to 6 carbon atoms, n is the number of moles of vinyl alcohol monomer, m is the number of moles of alkyl vinyl ether monomer, and the molar ratio, n/m, is from 98/2 to 80/20.

The PVA/AVE which is a copolymer used in the present invention is prepared by any processes including, for example, a process in which vinyl acetate and an alkyl vinyl ether are copolymerized according to known procedures and saponifying the resulting copolymer to a substantial complete extent.

R in the PVA/AVE of the formula (I) is an alkyl group such as methyl, ethyl, n-propyl, isopropyl, n-butyl, isobutyl, n-amyl, isoamyl, n-hexyl or the like. Of these, n-butyl is preferred in view of the film strength and flexibility. When R is H, the copolymer is identical to completely saponified PVA but is not preferred as a pack because its aqueous solution gels. On the other hand, the number of carbon atoms in R exceeding 7 is not favorable because of poor solubility in water.

In the practice of the invention, it is possible to suitably control the film strength and flexibility of PVA-/AVE by varying the molar ratio, n/m, of vinyl alcohol monomer and alkyl vinyl ether monomer. Thus, various types of packs can be prepared. The molar ratio, n/m, is preferred to range from 98/2 to 80/20. Within a range of from 95/5 to 85/15, there can be obtained copolymers having very high flexibility. In case where $(m/(m+n)) \times 100$ is less than 2, the resulting copolymer is unfavorable because of the gelation of the aqueous solution thereof. On the other hand, when $(m/(m+n)) \times 100$ exceeds 20, solubility in water of the resulting polymer becomes very poor.

The PVA/AVE used in the present invention in which the average molecular weight exceeds 200,000 is not favorable because its aqueous solution becomes cloudy. On the other hand, when the average molecular weight is less than 30,000, the resulting copolymer is unfavorable though soluble in water but poor in film-forming property.

The thus obtained PVA/AVE has, in the molecule thereof, no acetic groups with ester bonds. Instead, there are alkyl or alkenyl groups having ether bonds which serve for steric hindrance for preventing gelation of an aqueous solution of such copolymer. The PVA/AVE does not undergo any hydrolysis as time passes and is thus excellent in storage stability. More particularly, as will be seen in Examples appearing hereinafter, no change in pH or odor is recognized after storage at 50° C. for one month. When PVA/AVE used in the present invention is dissolved in water to prepare an aqueous solution, the solution has low viscosity, is good in coverability, and can be uniformly and readily coated onto skin. Because of the low viscosity, the concentration of the PVA/AVE can be increased to such an extent that with known PVA, it would be substantially impossible to use because of the high viscosity on dissolution in water. As a consequence, the drying time can be shortened when such PVA/AVE is added to film-forming cosmetics.

Aside from the essential PVA/AVE the film-forming cosmetics of the invention may further comprise various ingredients ordinarily used for these purposes, including, for example, film-forming agents such as hydroxyethyl cellulose, sodium carboxymethyl cellulose, various gums and the like; humectants such as glycerine, propylene glycol, polyethylene glycol, ethylene glycol, 1,3-butylene glycol, dipropylene glycol, diglycerine, hexylene glycol and the like; powders such as kaolin, talc, titanium oxide, iron oxide, zinc oxide, anhydrous silicic acid, magnesium carbonate and the like; oily ingredients such as olive oil, squalane, liquid paraffin, lanolin, vaseline and the like; alcohols and water; and, if necessary, surface active agents, medical agents, preservatives, perfumes, colorants and the like.

Preferable compositions of the film-forming cosmetics according to the invention are as follows.

|  | Preferable Range | Most Preferable Range |
|---|---|---|
| PVA/AVE | 1 to 40 (%) | 5 to 30 |
| Humectant | 1 to 20 | 5 to 15 |
| Powder Ingredient | 0 to 15 | 0 to 10 |
| Oily Ingredient | 0 to 8 | |
| Alcohol | 0 to 15 | |
| Surface Active Agent | 0 to 6 | |
| Purified Water | 30 to 70 | |
| Perfume, Colorant, Medical Agent, Preservative | each 0 to 1 | |

The thus obtained cosmetics of the invention are in the form of a uniform paste or liquid with no lowering of pH as a function of time and with good storage stability without involving deterioration with regard to odor. In addition, because of the low viscosity, they have good coverability and can be uniformly applied and dried within a short time.

The PVA/AVE used in the practice of the invention is very useful as film-forming agents of packs as described above and may have wide utility in various fields of, for example, film-forming agents of cosmetics such as nail enamels, eye liners, mascaras, hair dressings and the like, and thickners, emulsifiers and binders of cosmetics such as emulsions, foundations, creams, face powders, shampoos and the like.

Preferable types of the cosmetics of the present invention are aerosol packs. The conditions for the aerosolization of packs of the invention are as follows. The pressure in a container using propellants is controlled to range from 1 to 8 kg/cm$^2$, preferably from 2 to 7 kg/cm$^2$, at 20° C. If the pressure is less than 1 kg/cm$^2$, the content does not foam and is difficult to be injected from an aerosol can. Over 8 kg/cm$^2$, the injection from the can is vigorous and thus a difficulty encounters upon reception of the content on the hand with a problem of safety.

The propellants are not critical with respect to the type thereof. Typical of the propellants are compressed gasses such as nitrogen gas, nitrous oxide gas, carbon dioxide gas, argon gas and the like, and liquid propellants such as dichlorofluoromethane, trichloromonofluoromethane, dichlorotetrafluoroethane, liquefied petroleum gas and the like. These may be used singly or in combination.

The present invention is described by way of examples, synthetic examples and comparative examples.

SYNTHETIC EXAMPLE 1

Synthesis of Vinyl Alcohol/n-Butyl Vinyl Ether Copolymer 172.2 g (2.00 moles) of vinyl acetate, 15.1 g (0.15 mole) of n-butyl vinyl ether, 56.2 g of methanol and 0.28 g of 2,2'-azobis-2,4-dimethylvaleronitrile were mixed and polymerized in an atmosphere of N$_2$ at 62° C. for 8 hours. Subsequently, 749.2 g of 5% water-containing methanol and 8.0 g (0.20 mole) of caustic soda were added to the reaction product for saponification at 45° C. for 2 hours. The reaction mixture was milled and filtered to obtain a polymer portion, followed by washing with 5% water-containing alcohol to eliminate impurities such as sodium acetate therefrom. The purified polymer was dried under reduced pressure and milled to obtain 82.5 g of a white powdery vinyl alcohol/n-butyl vinyl ether (93/7 by molar ratio) copolymer (hereinafter referred to as PVA/n-BVE).

The thus obtained copolymer had a degree of saponification of 99.1 mole%, an average molecular weight of 74,000, and a residue of sodium acetate of 0.12 wt% (hereinafter referred to simply as %), with a viscosity of a 15% aqueous solution (at 25° C.) being 960 cps. The average molecular weight was calculated as follows: the copolymer obtained was acetylated and subjected to the gel permeation chromatography (GPC) to obtain a weight average molecular weight reduced to polystyrene (same as in the following Synthetic Examples and Examples).

SYNTHETIC EXAMPLES 2 TO 5

Vinyl acetate (VAc), n-butyl vinyl ether (n-BVE), methanol, 2,2'-azobis-2,4-dimethylvaleronitrile (V-65 of Wako Junyaku Co., Ltd.), 5% water-containing methanol, caustic soda were subjected to the process of Synthetic Example 1 using the weights indicated in Table 1, thereby obtaining copolymers of Synthetic Examples 2 to 5 indicated in Table 1. The copolymers of Synthetic Examples 2, 3 and Synthetic Examples 4, 5 were outside the scope of the invention with regard to molar ratio, n/m, and average molecular weight, respectively.

TABLE 1

| Synthetic Example | 2 | 3 | 4 | 5 |
|---|---|---|---|---|
| Weights of Feeds for Polymerization (g) | | | | |
| VAc | 86.1 | 86.1 | 86.1 | 86.1 |
| n-BVE | 1.0 | 26.6 | 5.3 | 5.3 |
| MeOH | 26.1 | 33.8 | 64.0 | 9.0 |
| V-65 | 0.26 | 0.34 | 0.46 | 0.18 |
| 5% Water-containing | | | | |

TABLE 1-continued

| Synthetic Example | 2 | 3 | 4 | 5 |
|---|---|---|---|---|
| MeOH | 348.4 | 450.8 | 365.6 | 365.6 |
| NaOH | 4.0 | 4.0 | 4.0 | 4.0 |
| PVA/n-BVE | | | | |
| Yield (g) | 38.3 | 53.0 | 38.5 | 37.0 |
| n/m (molar ratio) | 99/1 | 79/21 | 95/5 | 95/5 |
| Average Molecular Weight | 72000 | 70000 | 24000 | 220000 |
| Degree of Saponification (mole %) | 99.3 | 99.0 | 99.2 | 99.0 |
| Residual Sodium Acetate (%) | 0.10 | 0.18 | 0.21 | 0.20 |

EXAMPLE 1

Packs of the following formulations comprising the copolymer PVA/AVE of the invention and the comparative copolymers were prepared to compare these copolymers with regard to the pH and odor stabilities. The odor was evaluated according to the following evaluation standard. The results are shown in Table 2.

(Pack Composition)

| | |
|---|---|
| (1) Copolymer (Table 2) | 15(%) |
| (2) Propylene glycol | 5 |
| (3) Methylparaben | 0.1 |
| (4) Purified water | balance |

(Preparation)

(4) was heated to about 90° C., to which was added (1) portion by portion under agitation to give a uniform solution. Subsequently, (2) and (3) were added and agitated until uniformity was obtained, followed by cooling down to about 25° C. to give a product.

(Evaluation Standard)

O: Odorless
Δ: Slight odor of acetic acid
X: Odor of acetic acid

TABLE 2

| Pack | Test Item | Immediately After Preparation (Room Temp.) | After 0.5 Month Storage Temp. | | | After One Month Storage Temp. | | |
|---|---|---|---|---|---|---|---|---|
| | | | Room | 40° C. | 50° C. | Room | 40° C. | 50° C. |
| Product of Invention PVA/n-BVE | | | | | | | | |
| n/m = 93/7 | pH | 6.2 | 6.3 | 6.2 | 6.2 | 6.2 | 6.3 | 6.1 |
| Average Molecular Weight = 72,000 (Synthetic Example 1) | odor | O | O | O | O | O | O | O |
| Comparative Product PVA/PVAc | | | | | | | | |
| Average Degree of Polymerization = 2000 | pH | 6.0 | 6.1 | 6.0 | 5.1 | 6.0 | 5.8 | 4.9 |
| Degree of Saponification = 88 mole % | odor | O | O | O | X | O | Δ | X |

The results of the above test revealed that the pack of the invention comprising the PVA/AVE as the film-forming agent was better than the pack using known PVA/PVAc with regard to the pH and odor stabilities.

EXAMPLE 2

Packs of the same composition as in Example 1 were prepared except that copolymers used were indicated in the following Table 3 to compare them with regard to the viscosity and film properties. The results are shown in Table 3.

TABLE 3

| Pack | | Viscosity (cps) | Film Strength (dyne/cm²) | Flexibility (dyne/cm²) |
|---|---|---|---|---|
| Products of Invention | | | | |
| PVA/AVE | In Formula (I), R = n-butyl n/m = 95/5 Average Molecular Weight = 87,000 | 220 | $6.2 \times 10^8$ | $2.8 \times 10^8$ |
| | In Formula (I), R = n-butyl n/m = 90/10 Average Molecular Weight = 150,000 | 4,000 | $1.6 \times 10^8$ | $8.8 \times 10^7$ |
| | In Formula (I), R = iso-butyl n/m = 90/10 Average Molecular weight = 56,000 | 320 | $1.0 \times 10^8$ | $1.6 \times 10^8$ |
| Comparative Product | | | | |
| PVA/PVAc | Average Degree of Polymerization = 1900, Degree of Saponification = 88 mole % | 23,000 | $1.4 \times 10^8$ | $2.0 \times 10^8$ |

The above test results revealed that the packs of the invention comprising the PVA/AVE of the invention as the film-forming agent were not poorer than the pack using the known PVA/PVAc with respect to film properties and were characterized by low viscosity thereof.

COMPARATIVE EXAMPLE 1

Packs of the same composition as in Example 1 except that the comparative products obtained in Synthetic Examples 2 to 5 as the copolymer were prepared, thereby determining the state of the solutions and the state of the films obtained therefrom. The results are shown in Table 4.

TABLE 4

| Pack Copolymers | Test Item | |
|---|---|---|
| | State of Solution | State of Film |
| Synthetic Example 2 | gelled | — |
| Synthetic Example 3 | insoluble | — |
| Synthetic Example 4 | soluble | no film formed |
| Synthetic Example 5 | cloudy | — |

The test results revealed that the copolymers which were outside the scope of the present invention with regard to the molar ratio, n/m, and the average molecular weight were not favorable as the film-forming agent of the pack.

EXAMPLE 3

Packs of the following formulation using, as copolymer, the copolymer, PVA/AVE, of the invention and the comparative product. The packs were organoleptically assessed by 10 expert panels with regard to appearance and feeling to the touch. The assessment was based on the following evaluation standard. The results are shown in Table 5.

| (Pack Composition) | |
|---|---|
| (1) Copolymer (Table 5) | 15(%) |
| (2) Titanium oxide | 4 |
| (3) Ethylene glycol | 2 |
| (4) Ethanol | 10 |
| (5) Methylparaben | 0.1 |
| (6) Perfume | 0.2 |
| (7) Purified water | balance |

(Preparation)

(7) was heated to about 90° C., to which was added (1) portion by portion under agitation until uniformity was attained. Thereafter, (2) and (3) were added under agitation until uniformity was attained. When the mixture was cooled down to about 35° C., (4), (5) and (6) were added until uniformity was attained, followed by cooling to obtain a product.

| (Evaluation Standard) | |
|---|---|
| Very good | +2 |
| Good | +1 |
| Moderate | 0 |
| Poor | −1 |
| Very poor | −2 |

TABLE 5

| | Evaluation Item* | | | | |
|---|---|---|---|---|---|
| Pack | Appearance | Coverability | Ease or Difficulty of Uniform Application | Tightness of Pack | Ease or Difficulty of Separation (Peeling off) |
| Product of Invention | | | | | |
| PVA/n-BVE | | | | | |
| n/m = 93/7 | +0.1 | +1.5 | +1.7 | +1.8 | +0.7 |
| Average Molecular Weight = 84,000 | | | | | |
| Comparative Product | | | | | |
| PVA/PVAc | | | | | |
| Average Degree of Polymerization = 1700 | +0.3 | −0.1 | +0.2 | +1.1 | +0.3 |
| Degree of Saponiofication = 88 mole % | | | | | |

*The values in the table are each an average value of 10 persons.

The above test results revealed that the pack of the invention in which PVA/AVE was used as the film-forming agent was better in feeling to the touch than the pack using known PVA because of its better coverability, easier uniform application, formation of more uniform film.

EXAMPLE 4

Packs (A), (B) and (C) of the formulations indicated in Table 6 and using the copolymers PVA/AVE and a comparative copolymer were prepared for comparison with regard to drying time and viscosity. The results are shown in Table 7.

TABLE 6

| | Comparative Product | Product of Invention | |
|---|---|---|---|
| Pack | A | B | C |
| Composition (%) | | | |
| Copolymer | | | |
| PVA/PVAc | 15 | — | — |
| Average Degree of Polymerization = 2300 | | | |
| Degree of Saponification = 88 mole % | | | |
| PVA/n-BVE | | | |
| n/m = 97/3 | — | 20 | — |
| Average Molecular Weight = 70,000 | | | |
| PVA/n-BVE | | | |
| n/m = 97/3 | — | — | 30 |
| Average Molecular Weight = 50,000 | | | |
| Propylene Glycol | 5 | 5 | 5 |
| Ethanol | 10 | 10 | 10 |
| Water | 70 | 65 | 55 |

TABLE 7

| | Test Items | |
|---|---|---|
| | Drying Time (Minutes) | Viscosity (cps) |
| Pack (A) | 35 | 30,000 |
| Pack (B) | 25 | 13,000 |

TABLE 7-continued

| | Test Items | |
|---|---|---|
| | Drying Time (Minutes) | Viscosity (cps) |
| Pack (C) | 22 | 22,000 |

The above results revealed that the packs of the invention using PVA/AVE does not increase in viscosity and thus large amounts of the copolymers can be used, leading to an improvement of dryness.

EXAMPLE 5

A pack of the following formulation was prepared.

| (Formulation of Pack) | |
|---|---|
| (1) PVA/iso-BVE* n/m = 88/12 Average molecular weight = 120,000 | 15(%) |
| (2) Stearic acid | 6 |
| (3) Lanolin | 1 |
| (4) Glycerine | 1 |
| (5) Polyethylene glycol 1500 | 2 |
| (6) Glycerine monostearate | 3 |
| (7) Ethanol | 10 |
| (8) Purified water | balance |
| (9) Perfume | 0.2 |

*Copolymer of vinyl alcohol and isobutyl vinyl ether (Preparation)

(a) (2) to (6) were heated to 70° to 80° C. while agitating to obtain a uniform solution.

(b) To (8) of 20° to 30° C. was gradually added (1), followed by dispersion under agitation and dissolution at 80° C.

(b) was added to and well mixed with (a) under agitation. The mixture was cooled while continuedly agitating, followed by adding (7) and (9) at 30° to 35° C. to obtain a product.

The pack product had a low viscosity, good coverability and was ready to apply.

EXAMPLE 6

Aerosol packs of the following formulations were prepared.

| (Composition) | Aerosol A of Invention | Aerosol B for Comparison |
|---|---|---|
| (1) PVA/n-BVE (n/m = 93/7; average molecular weight 100,000) | 12.0 (%) | — |
| (2) PVA/PVAc (average degree of polymerization = 2,300; degree of saponification = 88 mole %) | — | 12.0 |
| (3) POE (60) hardened castor oil | 1.0 | 1.0 |
| (4) Coconut oil diethanolamide | 0.5 | 0.5 |
| (5) Glycerine | 3.0 | 3.0 |
| (6) Ethanol | 5.0 | 5.0 |
| (7) Perfume | 0.1 | 0.1 |
| (8) Purified water | balance | balance |

(Preparation)

(8) was heated to 90° C., to which was added (1) or (2) portion by portion under agitation to provide a uniform solution. Subsequently, (3), (4) and (5) were added and agitated to obtain a uniform mixture. After cooling down to about 35° C., (6) and (7) were added to obtain a uniform stock solution.

The thus obtained stock solutions were each filled in an aerosol can, which was then attached with a valve for aerosol, and a propellant was filled in the can to give a product. The inner pressure at 20° C. was controlled to be 3.5 kg/cm$^2$.

With the inventive product A, when used, the content was readily injected by application of the pressure from the propellant with a satisfactory degree of foaming. On the other hand, the comparative product B is so viscous that the content is difficult to be injected with an inadequate degree of foaming.

The inventive product A, the stock solution A' of the product A, and the stock solution B' of the comparative product B were tested to check their fluidity characteristic with the results shown in a sole FIGURE.

As will be apparent from the results, the inventive product A obtained by aerosolizing the composition of the invention exhibits a low shear stress at different shear rates with a small variation of the shear stress, so that the product can spread satisfactorily when applied. The product A is found to be different from a paste composition of the present invention with regard to fluidity.

What is claimed is:

1. A method of cosmetically treating skin, comprising:
    applying to the skin of a subject to be cosmetically treated, a cosmetic formulation containing from 1 to 40 weight percent of a copolymer consisting of 98–80 mole % of vinyl alcohol monomer units and 2–20 mole % of linear or branched alkyl vinyl ether monomer units having from 1 to 6 carbon atoms.

2. The method of claim 1, wherein the copolymer has an average molecular weight of 30,000 to 200,000.

3. The method of claim 1, wherein the molar ratio of the vinyl alcohol monomer units to the alkyl vinyl ether units ranges from 95/5 to 85/15.

4. The method of claim 1, wherein said composition is in the form of an aerosol pack which comprises, as a propellant, at least one compressed gas, at least one liquid propellant or a mixture thereof, so as to bring the pressure in the container of said pack containing said composition to within the range of from 1 to 8 kg/cm$^2$ at 20° C.

5. The method of claim 4, wherein said compressed gas is selected from the group consisting of nitrogen gas, nitrogen oxide gas, carbon dioxide gas and argon gas.

6. The method of claim 4, wherein said liquid propellant is a member selected from the group consisting of dichlorofluoromethane, trichloromonofluoromethane, dichlorotetrafluoroethane, and liquified petroleum gas.

* * * * *